United States Patent [19]

Rosenberg

[11] Patent Number: 4,850,375
[45] Date of Patent: Jul. 25, 1989

[54] URINE METER WITH TILTING GUIDE

[75] Inventor: Helmut W. G. Rosenberg, McHenry, Ill.

[73] Assignee: The Kendall Company, Boston, Mass.

[21] Appl. No.: 118,669

[22] Filed: Nov. 9, 1987

[51] Int. Cl.⁴ .............................................. A61B 5/00
[52] U.S. Cl. ...................................... 128/767; 604/322
[58] Field of Search ............... 128/760, 767, 768, 771; 604/318, 322–325, 335

[56] References Cited

U.S. PATENT DOCUMENTS

| Re. 30,607 | 5/1981 | Manschot et al. | 128/762 |
| 3,090,968 | 5/1963 | Buono | 4/110 |
| 3,383,017 | 5/1968 | Krings | 222/93 |
| 3,568,965 | 3/1971 | Clark | 248/95 |
| 3,604,420 | 9/1971 | Vaillancourt | 128/275 |
| 3,683,894 | 8/1972 | Villari | 128/771 |
| 3,776,231 | 12/1973 | Holbrook et al. | 128/275 |
| 4,000,649 | 1/1977 | Hanifl | 73/219 |
| 4,019,707 | 4/1977 | Quinn et al. | 248/95 |
| 4,095,589 | 6/1978 | Menschot et al. | 128/767 |
| 4,109,530 | 8/1978 | Kim | 73/427 |
| 4,114,640 | 9/1978 | Forman | 137/381 |
| 4,178,934 | 12/1979 | Forman | 128/771 |
| 4,219,177 | 8/1980 | O'Day | 248/215 |
| 4,254,771 | 5/1981 | Vidal | 128/275 |
| 4,305,290 | 12/1981 | Taylor | 73/427 |
| 4,305,405 | 12/1981 | Meisch | 128/767 |
| 4,417,891 | 11/1983 | Cianci | 128/767 |
| 4,447,939 | 5/1984 | Taylor | 128/760 |
| 4,449,969 | 5/1984 | Schweizer | 128/760 |
| 4,562,984 | 8/1983 | Sherlock et al. | 248/95 |
| 4,579,126 | 4/1986 | Cianci | 128/767 |
| 4,658,834 | 4/1987 | Blankenship et al. | 604/318 |
| 4,728,324 | 3/1988 | Steigerwald et al. | 604/335 |
| 4,731,062 | 3/1988 | Gross et al. | 604/325 |

Primary Examiner—Max Hindenburg
Attorney, Agent, or Firm—Emrich and Dithmar

[57] ABSTRACT

A urine meter comprising, a receptacle having a wall defining a cavity and an opening at the top of the receptacle communicating with the cavity, with the receptacle having a pair of opposed projections. The meter has a container having a front flexible wall and a back flexible wall, said front and back walls being formed together around their periphery to define a chamber in the container, said front wall being secured adjacent the top of the receptacle and having an opening communicating with the chamber and the cavity through the receptacle opening, said back wall extending over said container opening. The urine meter has a pair of forwardly directed guide members having a pair of elongated slots to receive the projections, such that the receptacle may be moved from a first lower upright position to collect liquid in the cavity to a second upper tilted portion to dump collected liquid from the cavity into the chamber.

2 Claims, 11 Drawing Sheets

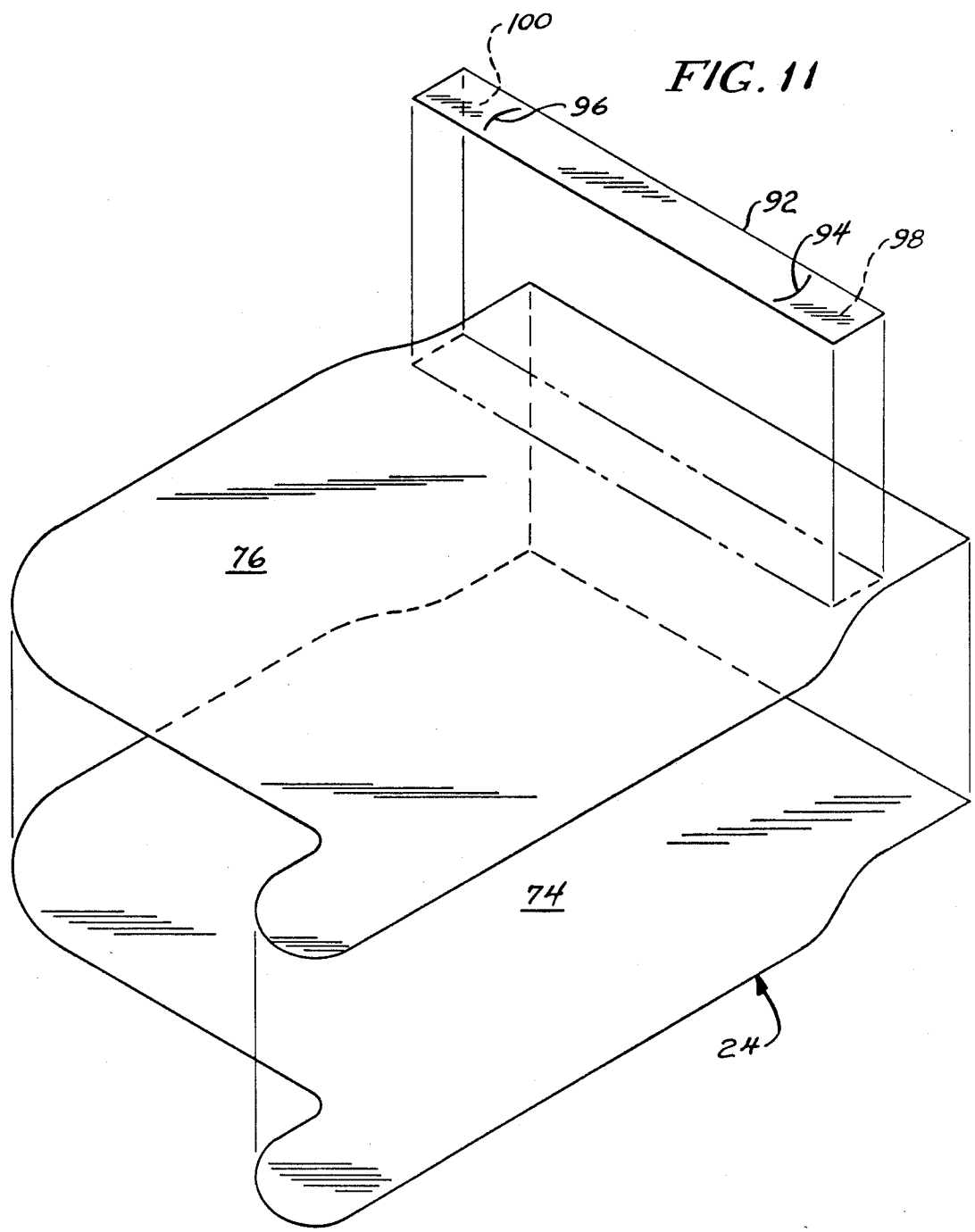

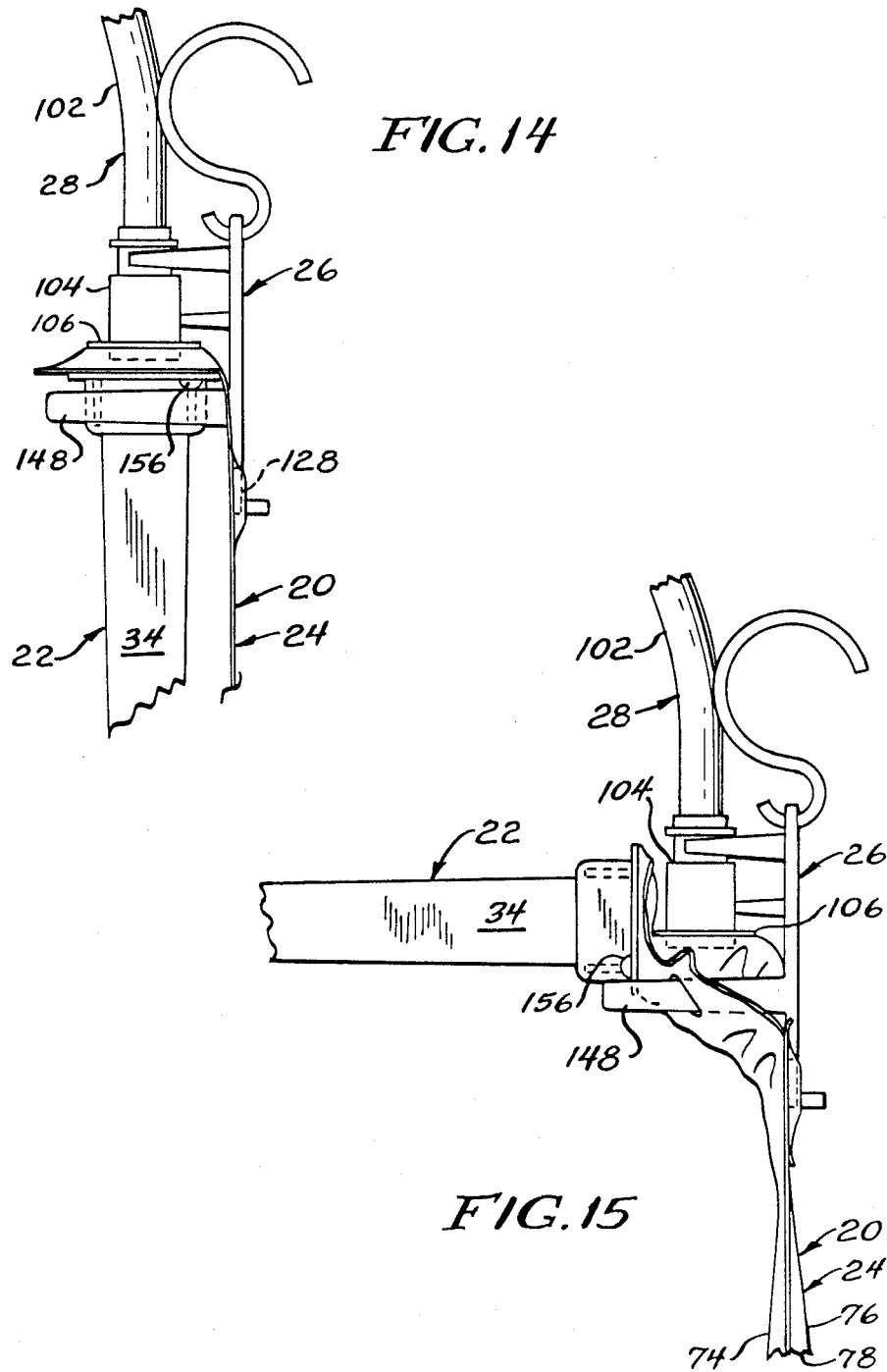

URINE METER WITH TILTING GUIDE

BACKGROUND OF THE INVENTION

The present invention relates to devices for collecting urine.

In the past, urine meters for collecting urine from a patient have been known. After catheterization of the patient, urine drains from the bladder through a catheter and drainage tube connected to the catheter into the urine meter. Conventionally, the urine meter has a front rigid receptacle and a rear flexible bag. The urine passes initially from the drainage tube into the receptacle for collection therein, with the receptacle providing a more accurate measurement of the collected urine than the bag. If the receptacle is not emptied into the bag for an extended period of time, the receptacle becomes full, and urine overflows from the receptacle into the bag. In a preferred form, however, the receptacle is periodically emptied manually into the bag prior to overflow and after urine measurement has taken place in the receptacle.

Although prior urine meters have operated satisfactorily in collecting urine, difficulties have been posed by the manner in which the receptacle is emptied into the bag. First, in many cases the urine meters require a complicated or confusing procedure to accomplish such emptying. Second, the structure of the prior urine meters have required an excessive amount of time to empty the receptacle into the bag which results in a great deal of inconvenience to hospital personnel.

SUMMARY OF THE INVENTION

A principal feature of the present invention is the provision of an improved urine meter.

The urine meter of the present invention comprises, a receptacle having a wall defining a cavity and an opening at the top of the receptacle communicating with the cavity. The urine meter has a container having flexible walls defining a chamber, with the container being secured to the top of the receptacle and having an opening communicating with the chamber and the cavity through the receptacle opening. The urine meter has inlet conduit means extending through the container to a position aligned with the cavity for draining liquid into the cavity. The urine meter has means for movably mounting the receptacle between a first lower upright position, and a second upper tilted position.

A feature of the present invention is that in the first upright position the receptacle collects liquid in the cavity.

Another feature of the present invention is that in the upper tilted position the liquid collected in the receptacle is dumped from the cavity into the chamber.

Yet another feature of the present invention is that the receptacle is emptied into the container in a simplified manner.

Another feature of the invention is that the opening of the receptacle extends the width an length of the receptacle.

A further feature of the invention is that the receptacle is emptied into the container considerably more quickly than the urine meters of the prior art.

A feature of the invention is that the receptacle may have a pair of opposed projections, and the urine meter has a support member having a pair of forwardly directed guide members with elongated slots to slidably receive the projections and positively guide the receptacle during tilting.

Further features will become more fully apparent in the following description of the embodiments of this invention and from the appended claims.

DESCRIPTION OF THE DRAWINGS

In the drawings:

FIG. 11 is an exploded perspective view showing construction of the container;

FIG. 14 is a fragmentary side elevational view of the urine meter of FIG. 13;

FIG. 15 is a fragmentary side elevational view of the urine meter of FIG. 13 with a front receptacle being dumped into a rear container;

DESCRIPTION OF THE PREFERRED EMBODIMENTS

Figure 1:
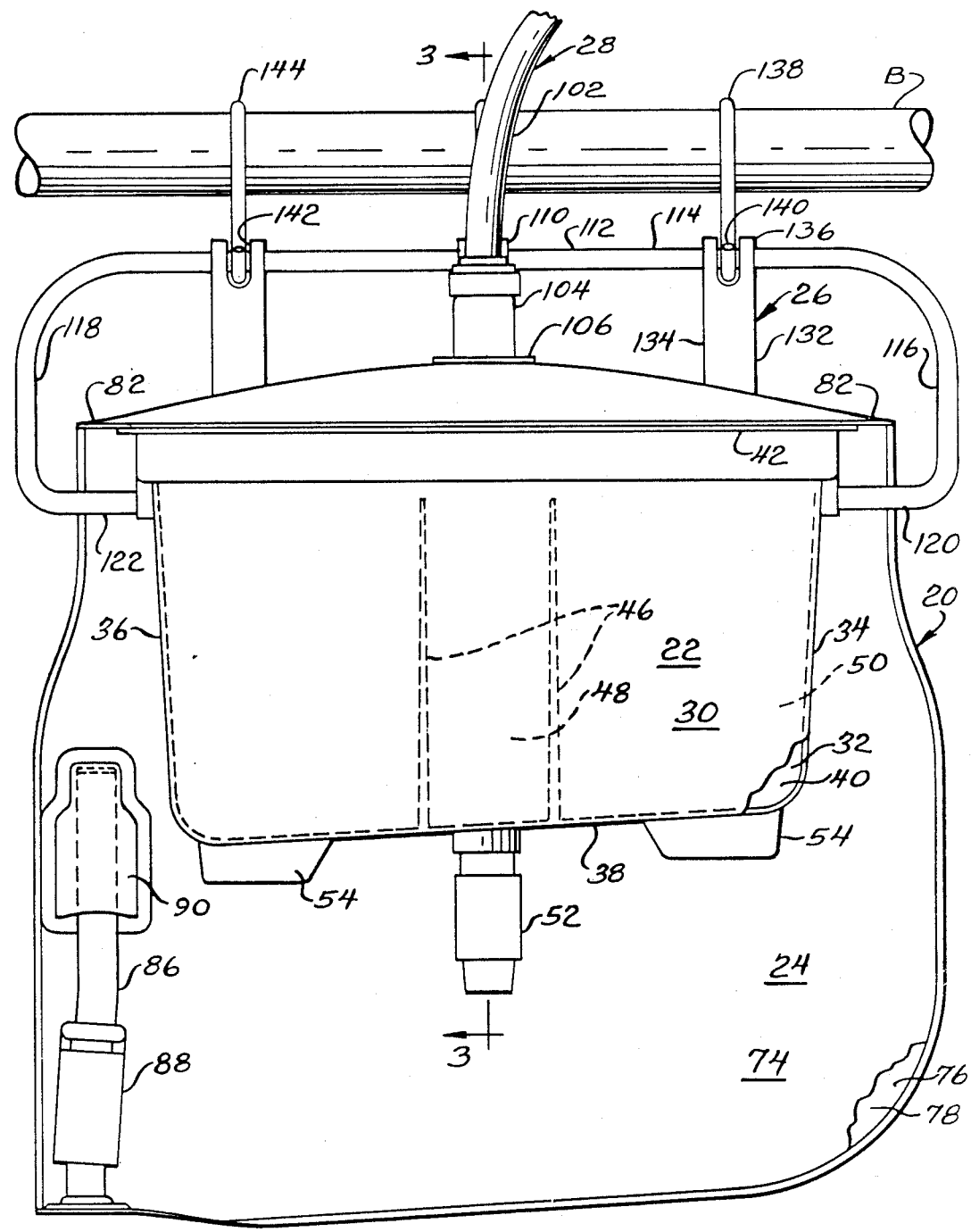
FIG. 1 is a fragmentary front elevational view of a urine meter.
Figure 2:
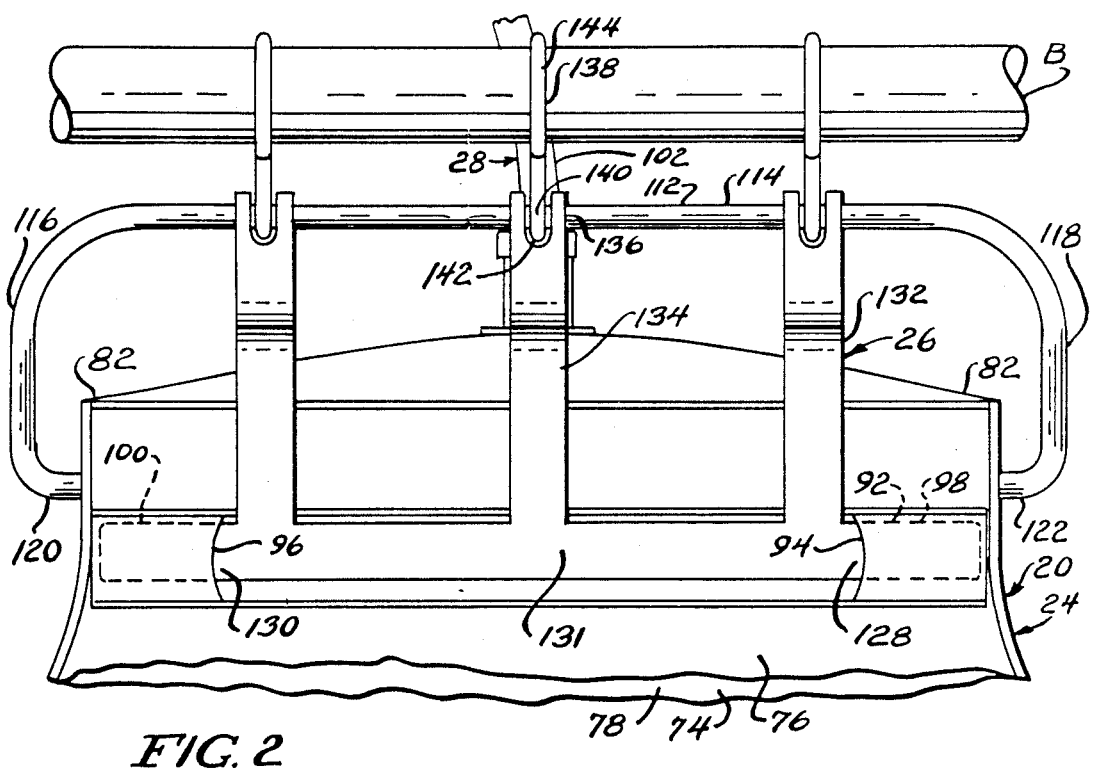
FIG. 2 is a fragmentary back elevational view of the urine meter of FIG. 1.
Figure 5:
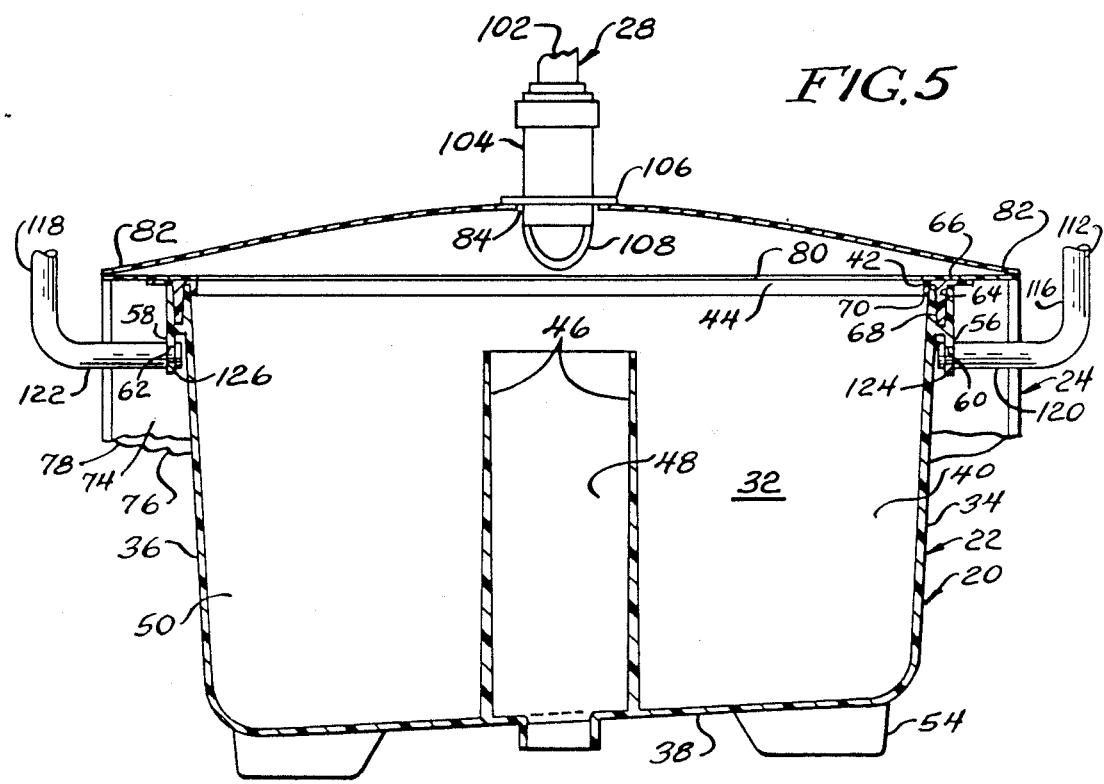
FIG. 5 is a fragmentary sectional view taken substantially as indicated along the line 5—5 of FIG. 4.

Referring now to FIGS. 1–5, there is shown a urine meter generally designated 20 having a front rigid receptacle 22, a rear flexible container 24, a support member 26, and inlet conduit means 28. The receptacle 22 may be made of any suitable rigid plastic material which is transparent. The container 24 may have walls constructed from any suitable flexible plastic material.

The receptacle 22 has a front wall 30, a rear wall 32, a pair of side walls 34 and 36 at opposed sides of the receptacle 22, and a bottom wall 38 defining a cavity 40 in the receptacle 22. The receptacle 22 has a top 42 defining an elongated opening 44 at the top 42 communicating with the cavity 40. The receptacle 22 has walls 46 extending from the front wall 30 and the bottom wall 38 defining an inner central first compartment 48, with the upper portion of the walls 46 being spaced from the top 42 of the receptacle 22, and with the walls 46 being spaced from the rear wall 32. The receptacle 22 has a second outer compartment 50 of the cavity 40 located on opposed sides of the inner compartment 48, behind the inner compartment 48, and above the inner compartment 48. As shown in FIG. 1, the bottom wall 38 is slanted downwardly from the side wall 34 to the side wall 36. In use, urine is initially directed into the small inner compartment for more accurate volume measurement by indicia on the front wall 30, and urine is permitted to overflow over the upper portion of the walls 46 into the outer compartment 50 of the cavity 40 where volume measurement may be made by indicia on the front wall 30. The overflow of urine flows in the outer compartment 50 toward the side wall 36 due to the slanted bottom wall 38 to obtain a more accurate determination of the initial portion of the overflow. The receptacle 22 has a lower valve 52 of known type communicating with the inner compartment 48, in order to drain urine from the inner compartment 48 during use of the urine meter 20 to obtain a fresh sample of urine. The receptacle 22 has a pair of lower depending lift tabs 54 to facilitate movement of the receptacle 22 relative to the container 24, as will be further discussed below.

Figure 9:
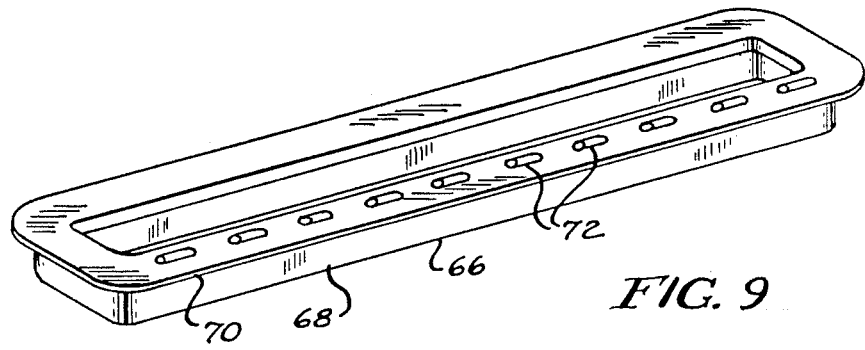
FIG. 9 is a perspective view of a retaining member for the receptacle.
Figure 12:
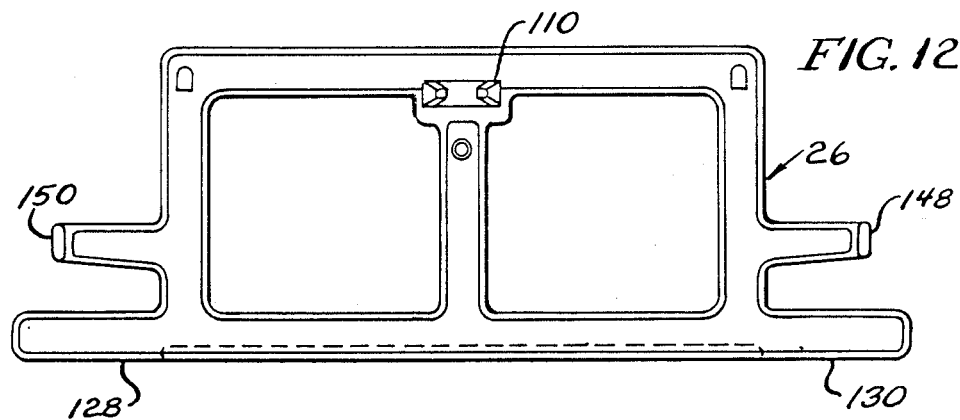
FIG. 12 is a front elevational view of a support member for another embodiment of the urine meter.

The receptacle 22 has a pair of depending flanges 56 and 58 adjacent an upper portion of the side walls 34 and 36, with the flanges 56 and 58 having respective apertures 60 and 62 extending therethrough for a purpose which will be described below. The receptacle 22 has an elongated channel 64 in the walls of the receptacle 22 at the upper portion of the receptacle 22 extending peripherally around the receptacle 22. With reference to FIGS. 1-5, and 9, the receptacle 22 preferably has an elongated retaining member 66 having a first downwardly directed annular flange 68 received in the channel 64. The retaining member 66 has a second outwardly directed flange 70 at the upper end of the first flange 68, such that the second flange 70 is located at the top 42 of the receptacle 22 when the retaining member 66 is received in the channel 64. As shown in FIG. 9, in a preferred form, the rear portion of the second flange 70 has a plurality of raised and spaced upper bosses 72 extending along the rear portion of the retaining member 66 for a purpose which will be described below.

Figure 3:
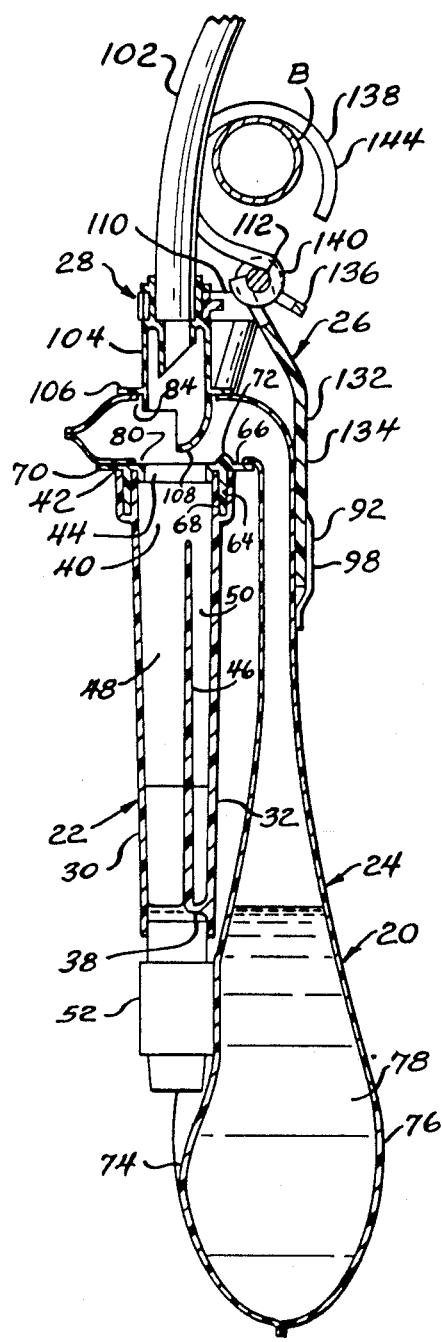
FIG. 3 is a fragmentary sectional view taken substantially as indicated along the line 3—3 of FIG. 1.

With reference to FIGS. 1-5, the container 24 has a flexible front wall 74, and a flexible rear or back wall 76, with the walls 74 and 76 being joined at their periphery in order to define a chamber 78 between the walls 74 and 76. In a preferred form, as shown, the container 24 extends to a location substantially below the receptacle 22 in order that the lower portion of the container 24 may bulge significantly during collection of urine in the container 24 without affecting the position of the receptacle 22, as shown in FIG. 3.

With reference to FIGS. 1-5, an upper portion of the front wall 74 is secured by suitable means, such as by adhesive or heat sealing, to the second flange 70 of the receptacle retaining member 66, with the front wall 74 having an elongated opening 80 aligned with the receptacle opening 44, such that the opening 80 communicates with the cavity 40 of the receptacle 22 through the opening 44 and the chamber 78 of the container 24. In this configuration, an upper portion of the rear wall 76 extends over the openings 44 and 80 of the receptacle 22 and container 24 above the top 42 of the receptacle 22, with the remaining portion of the container 24 depending from the top 42 of the receptacle 22 behind and below the receptacle 22. In this configuration, the receptacle 22 and container 24 are closed to the atmosphere, since the container 24 is sealed around the periphery of the opening 80 to the receptacle 22. In a preferred form, as shown, side portions 82 of the front and back walls 74 and 76 extend for a distance past the opposed sides of the receptacle 22 for a purpose which will be described below.

The rear wall 76 of the container 24 has an aperture 84 located above the openings 44 and 80 of the receptacle 22 and container 24 which will be further described below. The container 24 has a tubular section 86 communicating with the chamber 78 at a lower portion of the front wall 74, with the tubular section 86 being releasably closed by a clamp 88 of known type to drain urine from the container 24. In a storage position of the tubular section 86, an upper end of the tubular section 86 is releasably received in a pocket 90 on the front wall 74.

Figure 19:
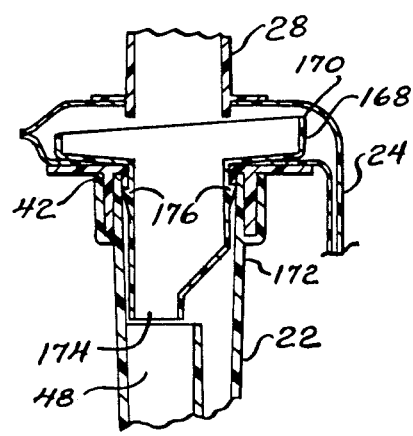
Figure 20:
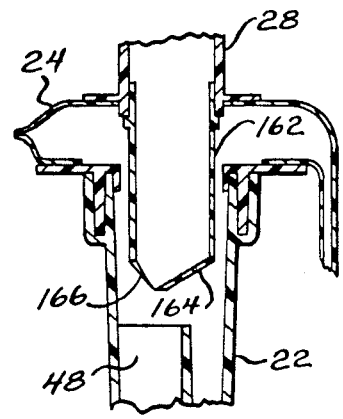
Figure 21:
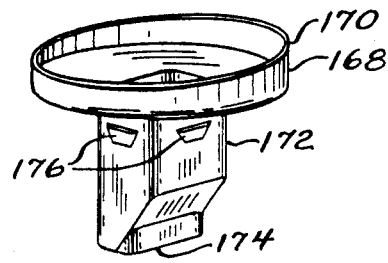
FIG. 21 is a prespective view of a funnel for the urine meter of FIG. 19.

With reference to FIGS. 1-5, and 11, the rear wall 76 of the container 24 has an elongated flexible strip 92 secured to the rear wall 76 and extending across the rear wall 76. The strip 92 may be heat sealed around its edges to the rear wall 76. The strip 92 is located slightly below the top 42 of the receptacle 22, and has a pair of elongated curved slits 94 and 96 extending partially across the strip 92 to define a pair of opposed pockets 98 and 100 communicating with the slits 94 and 96 intermediate the strip 92 and rear wall 76 for a purpose which will be described below The conduit means 28 has an elongated hollow drainage tube 102 communicating with and connected to a drip chamber 104, with the drip chamber 104 extending through the aperture 84 of the rear wall 76, and being connected to the rear wall 76 by a sealing ring 106 in fluid tight relationship in order to close the container chamber 78 to the atmosphere. The drip chamber 104 has a lower curved directing portion 108 in order to direct incoming liquid from the drip chamber 104 into the inner compartment 48 of the receptacle 22. Thus, the conduit means 28 has a lower portion located below the upper portion of the rear wall 76 in order to prevent passage of incoming liquid along the rear wall 76 directly into the container 24. The support member 26 has a clip 110 extending from the support member 26 and secured to the conduit means 28 adjacent an upper portion of the drip chamber 104. In the embodiment shown, the conduit means 28 is secured to the support member 26 at a location such that conduit means 28 raises the upper portion of the container rear wall 76 above the top 42 of the receptacle 22, such that the directing portion 108 of the drip chamber 104 is located above the openings 80 and 44 of the container 24 and receptacle 22. However, as shown in FIG. 20, the inner portion of the conduit means 28 may comprise an elastic tubular section 162 which extends through the openings 80 and 44 to a location above the inner compartment 48 to better insure the passage of urine directly into the inner compartment 48. The lower end of the tubular section 162 may include a deflecting member 164 leading to an opening 166 located above the inner compartment 48. In an alternative form, as shown in FIGS. 19 and 21, the conduit means 28 may have a lower funnel 168 positioned in the region of the receptacle top 42. The funnel 168 has an upper annular flange 170 connected to a hollow body portion 172 which tapers inwardly to an opening 174 located above the inner compartment 48. The funnel 168 is retained in position by a plurality of outwardly directed bosses 176 which grip the lower part of the retaining member 66 inside of the receptacle 22. Thus, the upper part of the funnel 168 is located above the receptacle top 42 to collect incoming urine, and the body portion 172 extends through the openings of the container and receptacle to a location above the inner compartment 48 to direct collected urine into the inner compartment 48.

The support member 26 has an elongated rod 112 which may be constructed of a suitable metal. The rod 112 has an upper central portion 114 located above the receptacle 22 and container 24 and extending slightly past the opposed sides of the receptacle 22, with the rod 112 having downwardly directed side portions 116 and 118 extending from the central portion 114. The rod 112 has lower inwardly directed opposed end portions 120 and 122 extending from the side portions 116 and 118 and directed towards the opposed sides of the receptacle 22, with the end portions 120 and 122 having annular outer grooves 124 and 126 adjacent ends of the rod 112 and pivotally received in the apertures 60 and 62 of the flanges 56 and 58 for a purpose which will be described below.

The support member 26 has a pair of lower opposed outwardly directed flanges 128 and 130 extending from a lower bar 131 and received in the pockets 98 and 100 in order to secure the support member 26 in fixed relationship to the rear wall 76 of the container 24. The support member 26 has a support portion 132 including the bar 131 and flanges 128 and 130, and including a plurality, such as three, upwardly directed retaining members 134 extending from the bar 131 and having upper turned ends 136 pivotally received on the central portion 114 of the rod 112. The support member 26 has a plurality of support hooks 138 associated with the retaining members 134, with the hooks 138 having a lower arcuate portion 140 pivotally received on the central portion 114 of the rod 112 through slots 142 of the upper turned ends 136, and an upper arcuate portion 144 removably received on a support device, such as a bed rail B in order to support the urine meter 20 from the bed rail B. In the described configuration, both the container 24 and receptacle 22 are supported by the support member 26 from the bed rail B during use of the urine meter 20.

In use, a patient is first catheterized with a catheter, such that a distal end of the catheter is located in the patient's bladder, and urine drains through the catheter to a proximal end of the catheter which is connected to an upstream end of the drainage tube 102, such that the urine drains through the drainage tube 102. From the drainage tube 102, the urine passes into the drip chamber 104, and the directing portion 108 of the drip chamber 104 directs the incoming urine into the inner compartment 48 with the receptacle 22 located in a first lower upright position. In the event that the receptacle 22 is not emptied for an extended period of time, the urine first fills the inner compartment 48, and overflows from the inner compartment 48 past the walls 46 into the outer compartment 50. Eventually, the outer compartment 50 is filled with urine, and the urine overflows from the cavity 40 through the opening 44 of the receptacle 22 and opening 80 of the container 24 into the chamber 78 of the container 24 where it is collected in the container 24.

Figure 6:
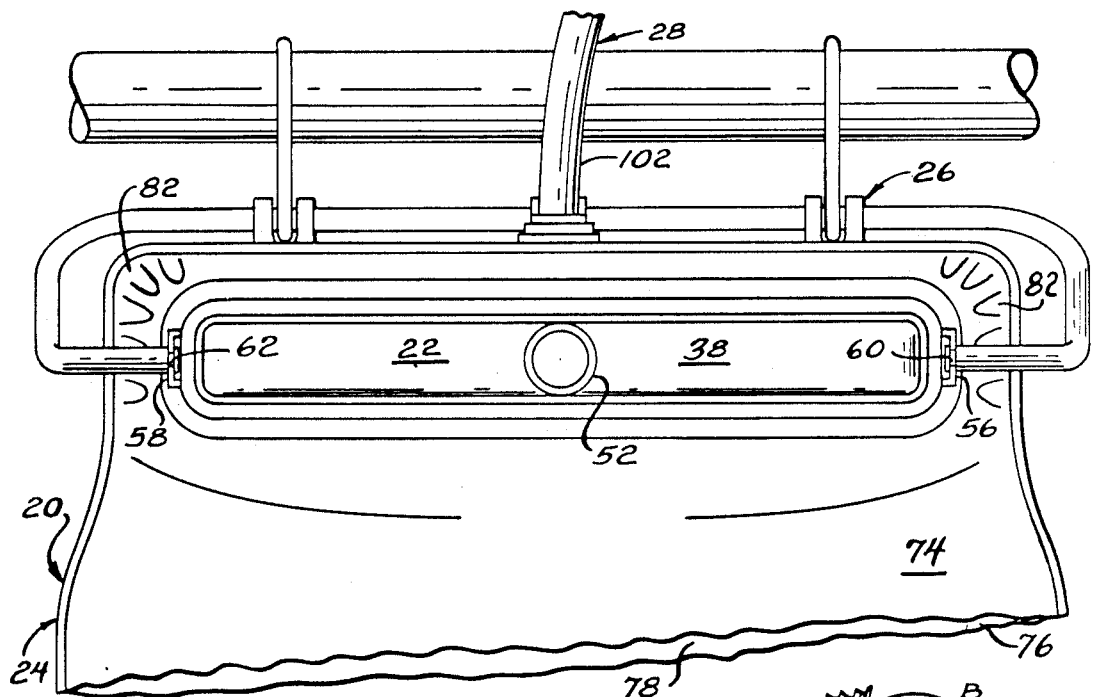
FIG. 6 is a fragmentary front elevational view showing a front receptacle being dumped into a rear container.
Figure 7:
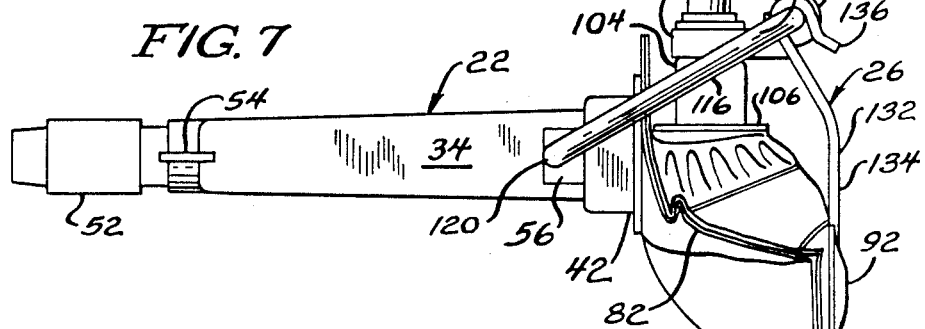
FIG. 7 is a fragmentary side elevational view of the receptacle being dumped into the container.
Figure 10:
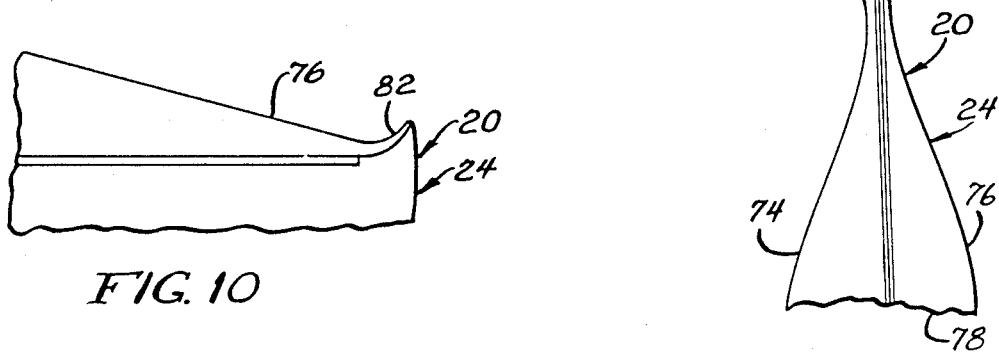
FIG. 10 is a fragmentary elevational view of a portion of the urine meter during dumping of the contents from the receptacle into the container.
Figure 8:
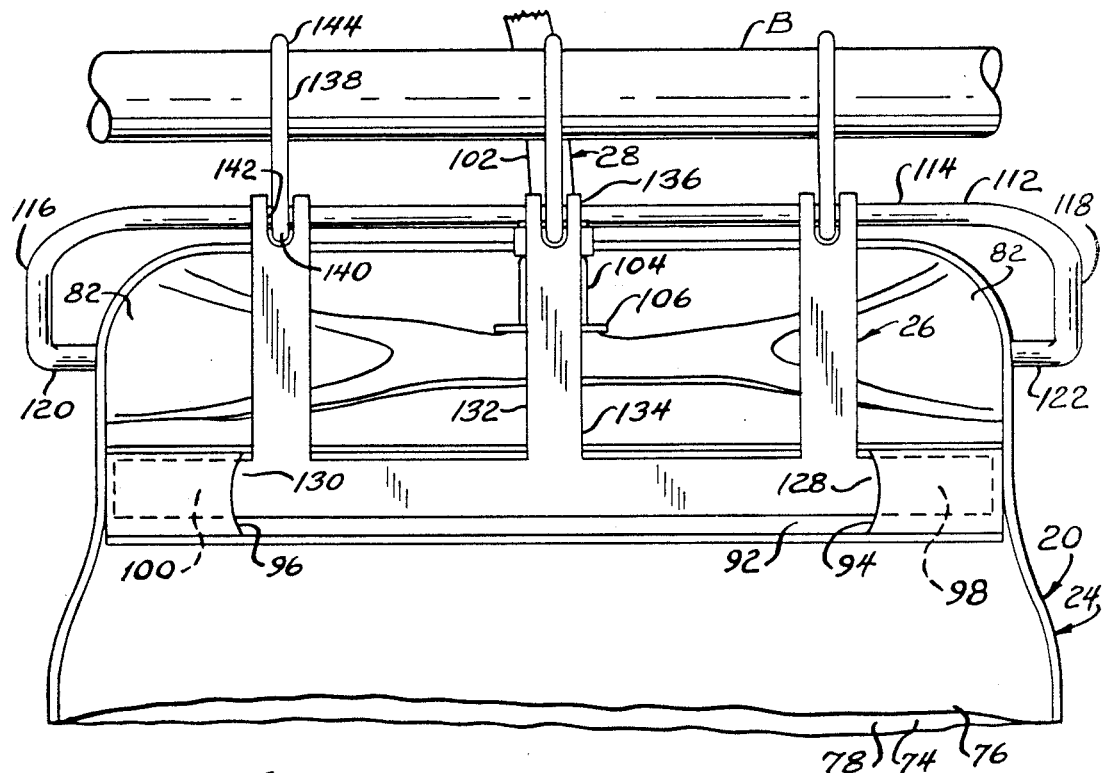
FIG. 8 is a fragmentary rear elevational view of the receptacle being dumped into the container.

However, in a preferred form, the urine is dumped from the receptacle 22 into the container 24 before the receptacle 22 overflows into the container 24. The urine is first measured in the receptacle 22 by suitable indicia (not shown) on the front wall 30 of the receptacle 22. Either before or after the urine overflows from the inner compartment 48 into the outer compartment 50, the lift tabs 54 of the receptacle 22 are manipulated by the hand in order to pivot the receptacle 22 on the rod 112 from the first lower upright position into a second upper tilted position, as shown in FIGS. 6–8, in which the receptacle 22 is approximately horizontal or slightly above the horizontal such that urine is dumped from the cavity 40 through the opening 44 of the receptacle 22 and the opening 80 of the container 24 into the container chamber 78. At the same time, the rod 112 is permitted to pivot in the retaining members 134 of the support member 26 in order to facilitate movement of the receptacle 22 to the upper tilted position. In the upper configuration of the receptacle 22, the side portions 82 of the container 24 flex upwardly, as shown in FIG. 10, and the rear will 76 gathers together caused by the extended side portions 82 about and below the openings 80 and 44 in order to insure that the rear wall 76 is spaced from the front wall 74 sufficiently to permit rapid passage of urine from the receptacle 22 into the container 24. Also, the conduit means 28 is fixed to the container rear wall 76 to also insure opening of the walls 74 and 76 during the dumping procedure.

Thus, in accordance with the present invention, the receptacle may be readily moved from the lower upright position to the raised tilted position in order to dump the contents of the receptacle 22 into the container 24. The dumping of urine meter 20 according to the present invention is accomplished in a simplified manner, and may be quickly completed through the relatively large openings 44 and 80 in order to save time by the hospital personnel during use of the urine meter 20.

As previously discussed, the support member 26 is attached to the rear wall 76 of the container 24 in a supporting relationship. Thus, when urine is introduced into the chamber 78 of the container 24, the weight of the collected urine is isolated from the connected receptacle 22 in order to prevent premature pivoting of the receptacle 22 which otherwise would cause outward upward movement of the receptacle 22 during collection which would be undesired. Also, during normal collection of urine with the receptacle 22 in the upright position, the bosses 72 on the retaining member 66 prevent sealing of the rear wall 76 against the retaining member 66 which might otherwise prevent normal overflow from the receptacle 22 into the container 24.

Figure 4:
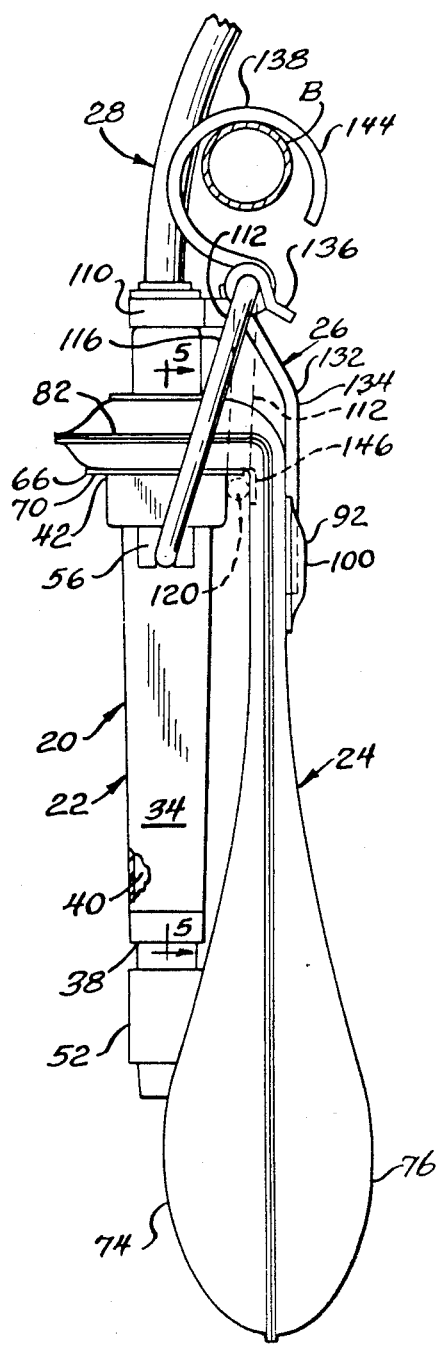
FIG. 4 is a fragmentary side elevational view of the urine meter of FIG. 1.

With reference to FIG. 4, in a slightly modified embodiment of the urine meter 20, as shown in dotted lines, the receptacle 22 has a rearwardly extending flange 146 partially extending around opposed ends of the rod 112, such that the rod 112 is pivotally connected to the receptacle 22 adjacent the rear wall 32 of the receptacle. In this configuration, the receptacle 22 is also pivotally mounted on the support member 26 for movement between the lower upright position to the upper tilted position in order to dump the contents of the receptacle 22 into the container 24.

Figure 16:
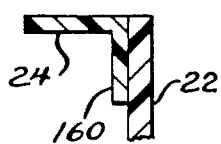
FIGS. 16–20 are fragmentary sectional views of alternate embodiments of the urine meter.
Figure 17:
Figure 18:
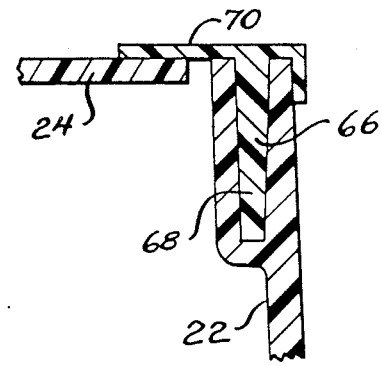

The container 24 has been described as being attached to the top 42 of the receptacle 22. In the presence of the retaining member 66, the container 24 is preferably secured to the upper part of the retaining member 66. However, in the absence of the retaining member 66, the receptacle 24 is preferably secured to the upper end of the receptacle walls. However, it should be understood that the container may be secured to sides of the receptacle walls in the region of the top 42. Thus, as shown in FIG. 16, the container 24 has a flange 160 secured to the upper portion of the receptacle 22 on the outer surface of the receptacle 22, while in FIG. 17 the flange 160 of the container 24 is secured to the upper portion of the receptacle 22 on the inner surface of the receptacle 22. With reference to FIG. 18, the container front wall 74 may be secured to the lower surface of the second flange 70 of the retaining member 66. In the various embodiments the container 24 is secured to the receptacle 22 adjacent the top 42 of the receptacle 22, including the top 42 of the receptacle 22.

Another embodiment of the urine meter 20 of the present invention is illustrated in FIGS. 12-15, in which like reference numerals designate like parts. In this embodiment, the urine meter 20 is similar in most respects to the urine meter described in connection with FIGS. 1-11 in that the upper portion of the container 24 is connected in fluid communication to the top of the receptacle 22. However, this embodiment of the urine meter 20 differs in the manner in which the support member 26 is constructed, and the manner in which the receptacle 22 is mounted on the support member 26. In this embodiment, the support member 26 also has a pair of outwardly directed lower flanges 128 and 130 received in pockets of the rear wall 76 of the container 24 in order to support the container 24 from the support member 26.

However, in this embodiment, the support member 26 has a pair of forwardly directed support flanges 148 and 150 extending through apertures 152 and 154 in the front and rear walls 74 and 76 of the container 24 to a location adjacent opposed sides of the receptacle 22, with the walls 74 and 76 being sealed around the apertures 152 and 154 to prevent leakage from the container 24 adjacent the apertures 152 and 154. The receptacle 22 has a pair of opposed outwardly directed bosses 156 and 158 extending from opposed sides of the receptacle 22 adjacent the rear of the receptacle 22, and resting on the respective support flanges 148 and 150.

Figure 13:
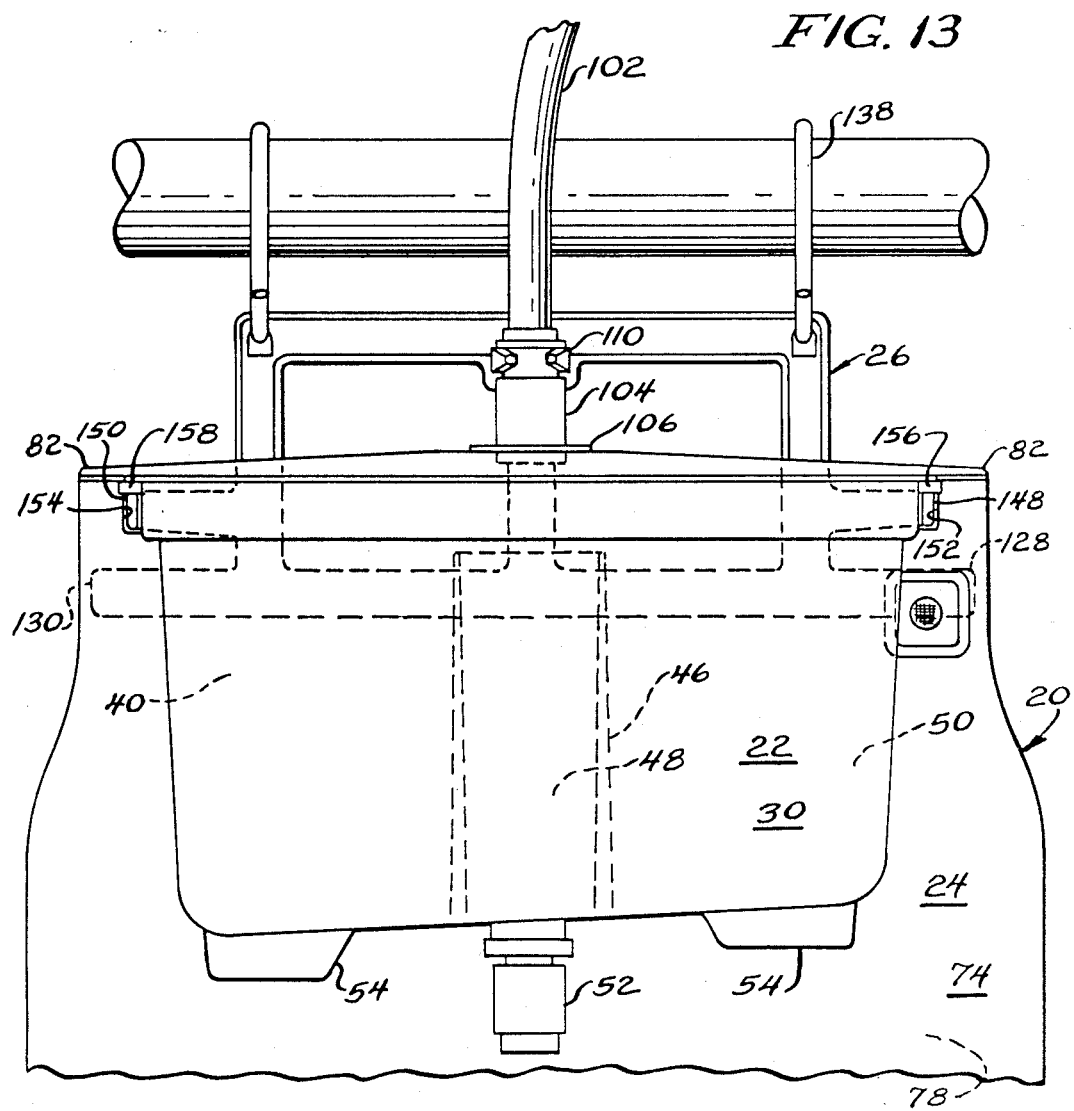
FIG. 13 is a fragmentary front elevational view of the second embodiment of the urine meter.

In the lower upright configuration of the receptacle 22, as shown in FIGS. 13 and 14, the bosses 156 and 158 are located adjacent a rear part of the support flanges 148 and 150. However, with reference to FIG. 15, when the receptacle is moved to its upper tilted position, the bosses 156 and 158 slide on the support flanges 148 and 150 to a location adjacent a forward portion of the support flanges 148 and 150. Thus, the receptacle 22 is slidably mounted on the support member 26 in order to accomplish movement of the receptacle 22 between the lower upright position and the tilted raised position for dumping the contents of the receptacle 22 into the container 24. In other respects, the urine meter 20 of FIGS. 12-15 is substantially the same as the urine meter 20 described in connection with FIGS. 1-11.

Another embodiment of the urine meter 20 of the present invention is illustrated in FIGS. 22-25, in which like reference numerals designate like parts. In this embodiment, the urine meter has an elastic band 180 having one end 182 secured in an opening 184 of the support member 26. The other end 186 is secured about a boss 188 extending from the side of the receptacle 22. The support member 26 has an outwardly directed flange 190 located near the top of the receptacle, and the band 180 extends through an opening 192 in the flange 190 and through openings 194 in the container 24 to the boss 188.

Figure 22:
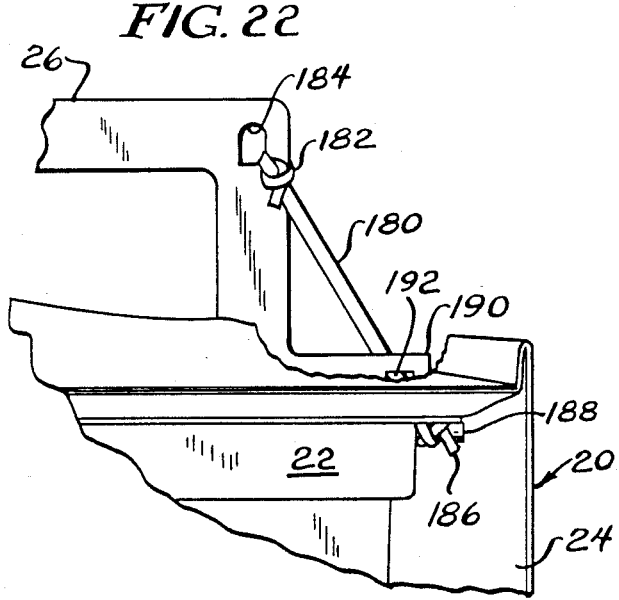
FIG. 22 is a fragmentary front elevational view of an alternate embodiment of the urine meter.
Figure 24:
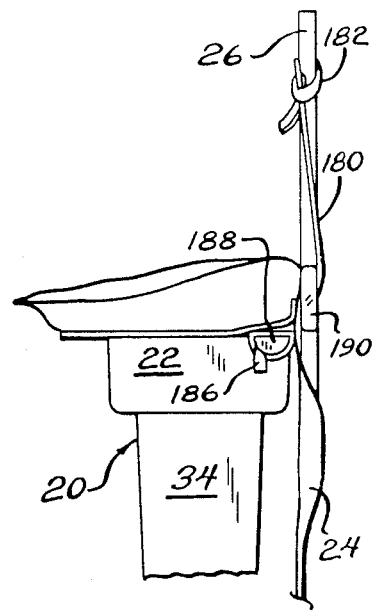
FIG. 24 is a fragmentary side elevational view of the urine meter of FIG. 22.
Figure 23:
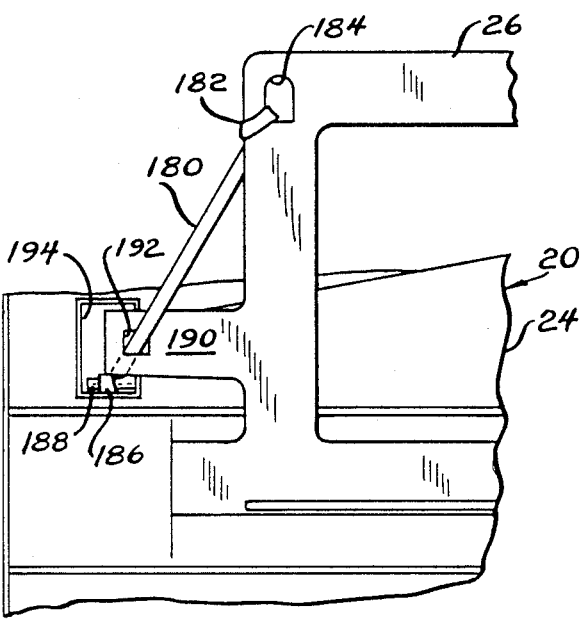
FIG. 23 is a fragmentary rear elevational view of the urine meter of FIG. 22.
Figure 25:
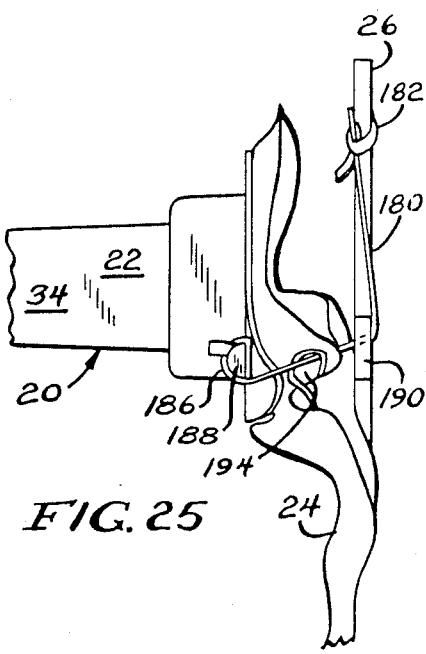
FIG. 25 is a fragmentary side elevational view of the urine meter of FIG. 22 with a front receptacle being dumped into a rear container.

When the receptacle 22 is located in the first lower upright position, as shown in FIGS. 22-24, the band 180 provides support for the receptacle with the band 180 being under slight tension. With reference to FIG. 25, when the receptacle is moved to the second upper tilted position, the band 180 is stretched, and thus biases the receptacle back toward the first upright position. Of course, the other side of the urine meter is substantially the same, as described in connection with FIGS. 22-25 Also, in other respects, the urine meter 20 of FIGS. 22-25 is substantially the same as the urine meter described in connection with FIGS. 1-21.

Figure 26:
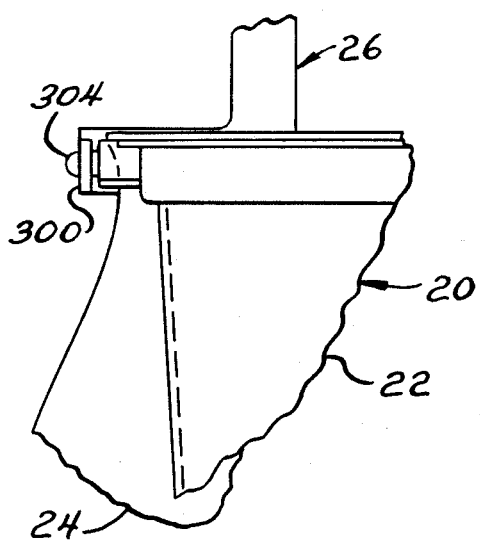
FIGS. 26–28 are fragmentary front and side elevational views of the urine meter of the present invention.
Figure 27:
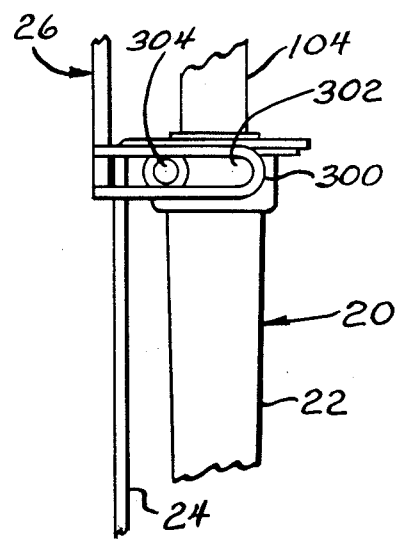
Figure 28:
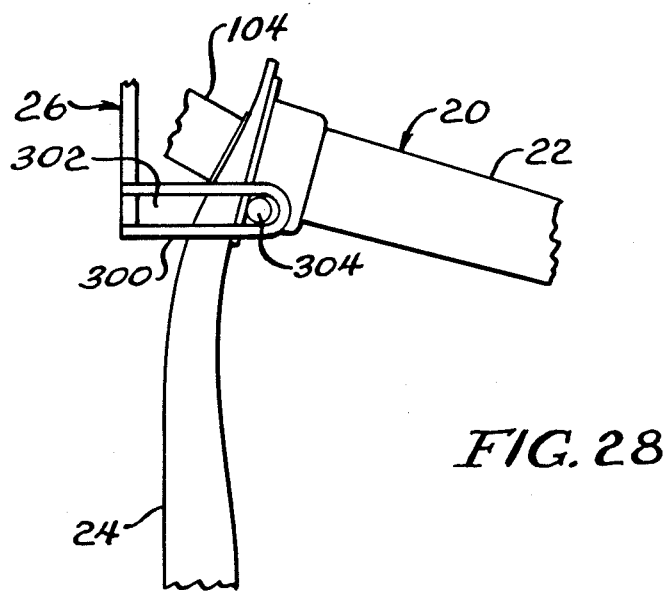

Another embodiment of the urine meter 20 of the present invention is illustrated in FIGS. 26-28, in which like reference numerals designate like parts. In this embodiment, the urine meter 20 is similar in most respects to the urine meter described in connection with FIGS. 1-11 in that the upper portion of the container 24 is connected in fluid communication to the top of the receptacle 22. However, this embodiment of the urine meter differs in the manner in which the support member 26 is constructed, and the manner in which the receptacle 22 is mounted on the support member 26.

In this embodiment, the support member 26 has a pair of forwardly directed guide members 300 having elongated slots 302 extending the length of the guide member 300. The receptacle 22 has a pair of opposed outwardly directed projections 304 slidably received in the slots 302.

In the lower configuration of the receptacle 22, as shown in FIGS. 26 and 27, the projections 304 are located adjacent a rear part of the guide members 300. However with reference to FIG. 28, when the receptacle is moved to its upper tilted position, the projections 304 slide in the slots 302 to a location adjacent a forward portion of the guide member 300. Thus, the receptacle 22 is slidably mounted in the guide members 300 in order to accomplish movement of the receptacle 22 between the lower upright position and the tilted raised position for dumping the contents of the receptacle 22 into the container 24, with the guide members 300 and projections providing positive control during the dumping operation. Of course, the other side of the urine meter is the same as shown in FIGS. 26-28. In other respects, the urine meter 20 of FIGS. 26-28 is substantially the same as the urine meter 20 described in connection with FIG. 1-11.

The foregoing detailed description is given for clearness of understanding only, and no unnecessary limitations should be understood therefrom, as modifications will be obvious to those skilled in the art.

What is claimed is:

1. A urine meter, comprising:
a receptacle having a wall defining a cavity and an opening at the top of the receptacle communicating with the cavity, said receptacle having a pair of opposed projections;
a container having a front flexible wall and a back flexible wall, said front and back walls being joined together around their periphery to define a chamber in the container, said front wall being secured adjacent the top of the receptacle and having an opening communicating with the chamber and the cavity through the receptacle opening, said back wall extending over said container opening; and a support member having a pair of forwardly directed guide members maintained in a fixed position relative to the support member and having a pair of elongated slots to receive the projections, such that the receptacle may be moved from a first lower upright position to collect liquid in the cavity to a second upper tilted position to dump collected liquid from the cavity into the chamber including inlet conduit means extending through an aperture in the back wall to a location below the back wall and aligned with the cavity, said conduit means being secured to the support member above the back wall.

2. The urine meter of claim 1 wherein the container is secured to the top of the receptacle.

* * * * *